US00PP18950P2

(12) United States Plant Patent
Lubbe

(10) Patent No.: US PP18,950 P2
(45) Date of Patent: Jun. 17, 2008

(54) ***PENSTEMON* PLANT NAMED 'RED RIDING HOOD'**

(50) Latin Name: *Penstemon schmidel*
Varietal Denomination: Red Riding Hood

(75) Inventor: Remy Lubbe, Noordwijkherhout (NL)

(73) Assignee: Molter B.V., Noordwijkherhout (NL)

( * ) Notice: Subject to any disclaimer, the term of this patent is extended or adjusted under 35 U.S.C. 154(b) by 0 days.

(21) Appl. No.: 11/728,155

(22) Filed: Mar. 16, 2007

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

PUBLICATIONS

UPOV ROM search for PBR 20051642. for cultivar Red Riding Hood. p.1.*

* cited by examiner

*Primary Examiner*—Annette H Para
(74) *Attorney, Agent, or Firm*—C. A. Whealy

(57) ABSTRACT

A new and distinct cultivar of *Penstemon* plant named 'Red Riding Hood', characterized by its upright and relatively compact plant habit; freely flowering habit; bright red-colored flowers arranged on strong flowering stems; and good garden performance.

1 Drawing Sheet

Botanical designation: *Penstemon schmidel.*
Cultivar denomination: 'Red Riding Hood'.

BACKGROUND OF THE INVENTION

The present invention relates to a new and distinct cultivar of *Penstemon,* botanically known as *Penstemon schmidel* and hereinafter referred to by the name 'Red Riding Hood'.

The new *Penstemon* is a product of a planned breeding program conducted by the Inventor in Noordwijkerhout, The Netherlands. The objective of the breeding program is to create new strong *Penstemon* cultivars with numerous attractive flowers and good garden performance.

The new *Penstemon* originated from a cross-pollination during the spring of 2001 of two unnamed selections of *Penstemon schmidel,* not patented. The new *Penstemon* was discovered and selected by the Inventor as a single flowering plant from within the progeny of the stated cross-pollination grown in a controlled environment in Noordwijkerhout, The Netherlands during the summer of 2002.

Asexual reproduction of the new cultivar by vegetative cuttings in Voorhout, The Netherlands, since the spring of 2004, has shown that the unique features of this new *Penstemon* are stable and reproduced true to type in successive generations.

SUMMARY OF THE INVENTION

Plants of the cultivar Red Riding Hood have not been observed under all possible environmental conditions. The phenotype may vary somewhat with variations in environment such as temperature and light intensity without, however, any variance in genotype.

The following traits have been repeatedly observed and are determined to be the unique characteristics of 'Red Riding Hood'. These characteristics in combination distinguish 'Red Riding Hood' as a new and distinct cultivar:

1. Upright and relatively compact plant habit.
2. Freely flowering habit.

3. Bright red-colored flowers arranged on strong flowering stems.
4. Good garden performance.

Plants of the new *Penstemon* differ from plants of the parent selections in the following characteristics:

1. Plants of the new *Penstemon* are more compact and stockier than plants of the parent selections.
2. Plants of the new *Penstemon* have stronger flowering stems than plants of the parent selections.
3. Flower color of plants of the new *Penstemon* is more intense red than flower color of plants of the parent selections.

Plants of the new *Penstemon* can be compared to plants of the cultivar Red Knight, not patented. In side-by-side comparisons conducted in Noordwijkerhout, The Netherlands, plants of the new *Penstemon* differed from plants of the cultivar Red Knight in the following characteristics:

1. Plants of the new *Penstemon* were more compact than plants of the cultivar Red Knight.
2. Plants of the new *Penstemon* were more freely branching than plants of the cultivar Red Knight.
3. Plants of the new *Penstemon* had stronger flowering stems than plants of the cultivar Red Knight.
4. Plants of the new *Penstemon* were more freely flowering than plants of the cultivar Red Knight.
5. Flower color of plants of the new *Penstemon* was more intense red than flower color of plants of the cultivar Red Knight.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Penstemon.* The photograph comprises a side perspective view of typical flowering plants of 'Red Riding Hood' grown in an outdoor nursery.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were grown under conditions which closely approximate commercial production conditions during the summer in an outdoor nursery in Noordwijkerhout, The Netherlands for about one year. During the production of the plants, day temperatures ranged from 20° C. to 33° C. and night temperatures ranged from 12° C. to averaged 20° C.

Botanical classification: *Penstemon schmidel* cultivar Red Riding Hood.

Parentage:

*Female parent.*—Unnamed selection of *Penstemon schmidel,* not patented.

*Male parent.*—Unnamed selection of *Penstemon schmidel,* not patented.

Propagation:

*Type cutting.*—Vegetative cuttings.

*Time to initiate roots.*—About eight to ten days at 20° C. to 22° C.

*Root description.*—Fine, fibrous; 161D in color.

*Rooting habit.*—Dense.

Plant description:

*Form.*—Upright and relatively compact plant form; narrow inverted triangle. Freely basal branching with about 16 main stems; vigorous growth habit.

*Plant height.*—About 60 cm.

*Plant width.*—About 25 cm.

*Lateral branch description.*—Length: About 60 cm. Diameter: About 3 mm. Internode length: About 4.8 cm. Strength: Strong. Texture: Smooth, glabrous. Color: 148A.

Foliage description:

*Arrangement.*—Opposite, simple; sessile.

*Length.*—About 7.8 cm.

*Width.*—About 2.1 cm.

*Shape.*—Lanceolate.

*Apex.*—Acuminate.

*Base.*—Truncate to oblique.

*Margin.*—Entire.

*Texture, upper and lower surfaces.*—Smooth, glabrous.

*Venation pattern.*—Pinnate.

*Color.*—Developing foliage, upper surface: 148A. Developing foliage, lower surface: 147A. Fully expanded foliage, upper and lower surfaces: 147A; venation, 136A.

Flower description:

*Flower arrangement and shape.*—Single bi-labiate flowers arranged on terminal racemes; flowers face mostly outwardly. Freely flowering, about 70 to 150 flowers developing per inflorescence.

*Fragrance.*—None detected.

*Natural flowering season.*—Plants flower during the summer in The Netherlands.

*Flower longevity on the plant.*—About two weeks; flowers not persistent.

*Flower buds.*—Length: About 6 mm. Diameter: About 4 mm. Shape: Ovoid. Color: 138B.

*Inflorescence size.*—Length: About 25 cm to 40 cm. Diameter: About 15 cm to 25 cm.

*Flowers.*—Diameter: About 2.4 cm. Depth (height): About 3.1 cm.

*Petals.*—Arrangement: Five, fused into a tube; bi-labiate, upper lip with two upper petals and lower lip with three lower petals. Length: About 6 mm. Width: About 4 mm. Shape: Ovate to obovate. Apex: Rounded. Margin: Entire. Texture, upper and lower surfaces: Smooth, glabrous; satiny. Color: When opening and fully opened, upper surface: 45B. When opening and fully opened, lower surface: 46C.

*Sepals.*—Arrangement: Four sepals, fused; calyx salverform. Length: About 3 mm. Width: About 2 mm. Shape: Round. Apex: Acute. Margin: Entire. Texture, upper and lower surfaces: Smooth, glabrous. Color: Immature and mature, upper surface: 147B. Immature and mature, lower surface: 148A.

*Peduncles.*—Strength: Very strong. Length: About 43 cm. Diameter: About 3 mm. Aspect: Upright to about 30° from vertical. Texture: Smooth, glabrous. Color: 138C.

*Pedicels.*—Strength: Strong. Length: About 1.8 cm. Diameter: About 1.5 mm. Aspect: About 10° from the peduncle axis. Texture: Smooth, glabrous. Color: 138B.

*Reproductive organs.*—Stamens: Quantity per flower: Four. Anther shape: Oval. Anther length: About 2 mm. Anther color: Close to 202A. Pollen amount: Scarce to moderate. Pollen color: 158B. Pistils: Quantity per flower: One. Pistil length: About 3.3 cm. Stigma shape: Somewhat conical. Stigma color: 155B. Style length: About 2.9 cm. Style color: 47C. Ovary color: 147B.

*Seed/fruit.*—Seed and fruit production has not been observed.

Disease/pest resistance: Plants of the new *Penstemon* have not been noted to be resistant to pathogens and pests common to *Penstemon.*

Garden performance: Plants of the new *Penstemon* have exhibited good tolerance to rain and wind and have been observed to tolerate temperatures ranging from about −10° C. to about 35° C.

It is claimed:

1. A new and distinct *Penstemon* plant named 'Red Riding Hood' as illustrated and described.

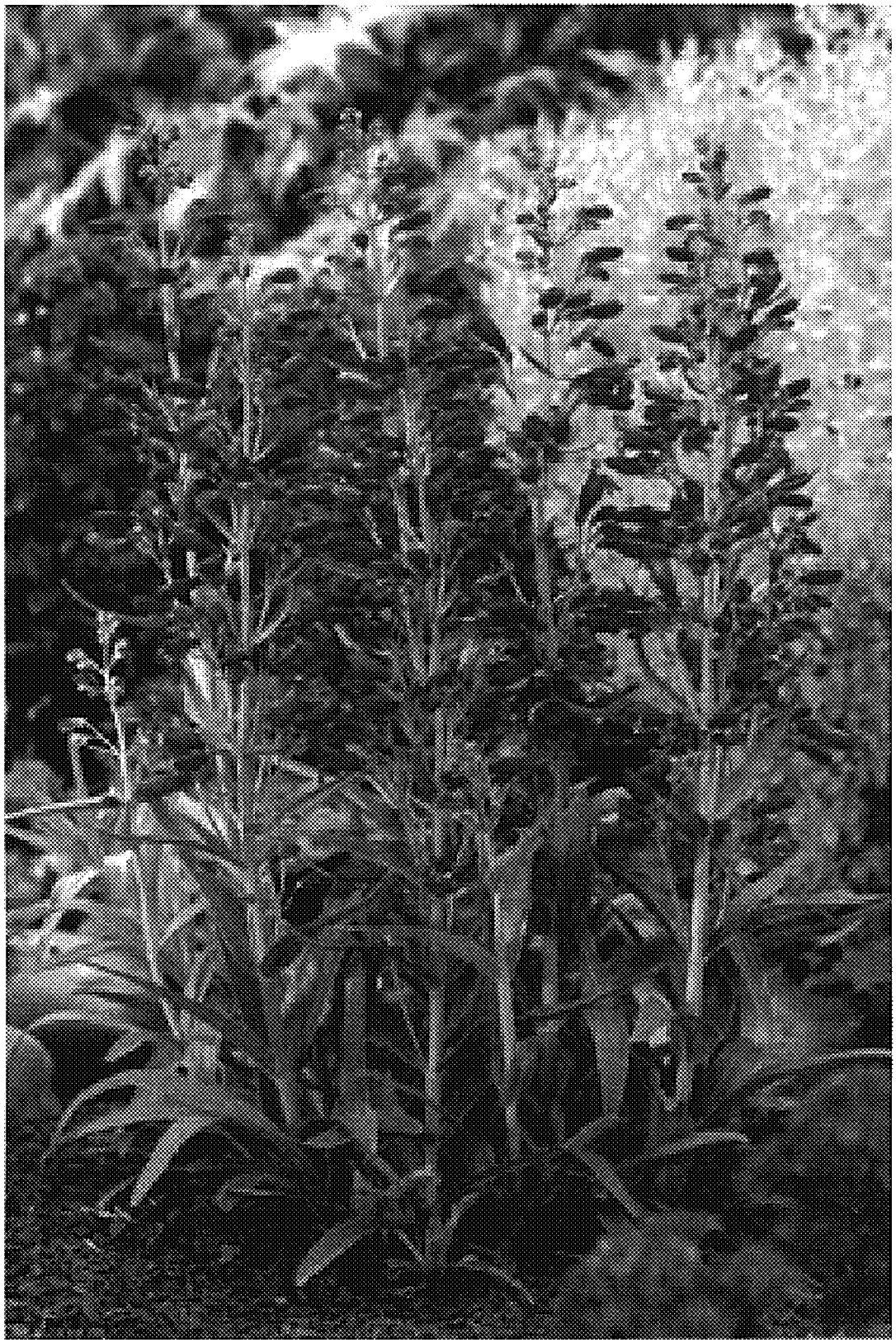

* * * * *